United States Patent
Reime

[11] Patent Number: 5,726,547
[45] Date of Patent: Mar. 10, 1998

[54] WINDSHIELD WIPER ARRANGEMENT INCLUDING WIPER CONTROL SYSTEM

[76] Inventor: Gerd Reime, Friedenstr. 88, D-75328 Schömberg, Germany

[21] Appl. No.: 578,683

[22] PCT Filed: Jun. 18, 1994

[86] PCT No.: PCT/DE94/00710

§ 371 Date: Jun. 17, 1996

§ 102(e) Date: Jun. 17, 1996

[87] PCT Pub. No.: WO95/01270

PCT Pub. Date: Jan. 12, 1995

[30] Foreign Application Priority Data

Jul. 2, 1993 [DE] Germany ............... 9309837 U
Feb. 3, 1994 [DE] Germany ............... 44 03 221.8
Apr. 6, 1994 [DE] Germany ............... 44 11 772.8

[51] Int. Cl.$^6$ .................................................. B60S 1/08
[52] U.S. Cl. ............................................. 318/483; 318/480
[58] Field of Search .................. 318/DIG. 2, 444, 318/483, 280, 281–286, 480

[56] References Cited

U.S. PATENT DOCUMENTS

| | | | |
|---|---|---|---|
| 4,542,325 | 9/1985 | Kobayashi et al. | 318/483 |
| 4,620,141 | 10/1986 | McCumber et al. | 318/483 |
| 4,916,374 | 4/1990 | Schierbeek et al. | 318/483 |
| 4,956,591 | 9/1990 | Schierbeek et al. | 318/483 |
| 4,960,996 | 10/1990 | Hochstein | 318/DIG. 2 X |
| 5,015,931 | 5/1991 | Muller | 318/483 |
| 5,059,877 | 10/1991 | Teder | 318/444 |
| 5,117,168 | 5/1992 | Nomura et al. | 318/444 |
| 5,140,233 | 8/1992 | Wallrafen | 318/DIG. 2 |
| 5,252,898 | 10/1993 | Nolting et al. | 318/DIG. 2 |

FOREIGN PATENT DOCUMENTS

| | | |
|---|---|---|
| 0 249 031 | 12/1987 | European Pat. Off. . |
| 0 408 304 | 1/1991 | European Pat. Off. . |
| 0 438 633 | 7/1991 | European Pat. Off. . |
| 0 520 302 | 12/1992 | European Pat. Off. . |
| 0 547 337 | 6/1993 | European Pat. Off. . |
| 0 562 275 | 9/1993 | European Pat. Off. . |
| 2 200 878 | 8/1973 | Germany . |
| 25 29 866 | 2/1976 | Germany . |
| 23 54 100 | 10/1976 | Germany . |
| 26 30 470 | 1/1978 | Germany . |
| 28 36 734 | 7/1979 | Germany . |
| 30 38 141 | 2/1982 | Germany . |
| 82 02 355 | 3/1983 | Germany . |
| 31 40 865 | 5/1983 | Germany . |
| 32 03 091 | 8/1983 | Germany . |
| 32 18 279 | 11/1983 | Germany . |
| 32 35 590 | 3/1984 | Germany . |
| 33 14 770 | 11/1987 | Germany . |

(List continued on next page.)

*Primary Examiner*—Brian Sircus
*Attorney, Agent, or Firm*—Spencer & Frank

[57] ABSTRACT

A windshield wiper arrangement which includes a windshield having a wiping area and a sensor-active surface on its wiping area. A wiper sweeps over the wiping area during a wiper operation. A wiper control system includes: a drive motor for driving the wiper; and a sensor system including a sensor disposed in the wiping area such that the wiper passes over the sensor n times during each wiper operation, n being equal to at least one, the sensor system further being configured for generating a sensor signal in response to an element coming into contact with the sensor-active surface on the windshield. The wiper control system further includes a signal processing device for generating the motor signal in response to the sensor signal which includes a counter arrangement having a counter for counting sensor signals generated by the sensor system thereby resulting in a counter state of the counter, the counter state of the counter further being equal to a predetermined starting value before each wiper operation. The signal processing device further includes an arrangement responsive to the counter state exceeding a predetermined threshold value for generating a motor signal for tripping each wiper operation, the threshold value being greater than n; and an arrangement for resetting the counter state to its starting value.

15 Claims, 6 Drawing Sheets

FOREIGN PATENT DOCUMENTS

| | | |
|---|---|---|
| 37 15 798 | 1/1988 | Germany . |
| 38 25 663 | 2/1989 | Germany . |
| 38 25 665 | 2/1989 | Germany . |
| 37 33 762 | 4/1989 | Germany . |
| 38 00 327 | 7/1989 | Germany . |
| 39 41 905 | 6/1990 | Germany . |
| 90 10 998 | 12/1990 | Germany . |
| 39 35 807 | 5/1991 | Germany . |
| 40 27 367 | 7/1991 | Germany . |
| 41 02 146 | 9/1991 | Germany . |
| 40 36 407 | 5/1992 | Germany . |
| 40 18 903 | 10/1992 | Germany . |
| 42 29 491 | 1/1993 | Germany . |
| 41 34 432 | 4/1993 | Germany . |
| 41 41 348 | 6/1993 | Germany . |
| 41 20 750 | 7/1993 | Germany . |
| 37 22 510 | 9/1993 | Germany . |
| 93 09 837 | 10/1993 | Germany . |
| 42 17 390 | 12/1993 | Germany . |
| 42 17 391 | 12/1993 | Germany . |
| 42 31 763 | 3/1994 | Germany . |
| 61-11637 | 1/1986 | Japan . |
| 2-38167 | 2/1990 | Japan . |
| 90/08680 | 8/1990 | WIPO . |
| 91/09756 | 7/1991 | WIPO . |

FIG. 10

WINDSHIELD WIPER ARRANGEMENT INCLUDING WIPER CONTROL SYSTEM

FIELD OF THE INVENTION

The invention relates to a windshield having a wiping area and a sensor-active surface on its wiping area; a wiper disposed adjacent the windshield for sweeping over the wiping area thereof during a wiper operation, the wiper further having a parking position; and a wiper control system operatively coupled to the wiper.

BACKGROUND OF THE INVENTION

One such device is known from German Patent Disclosure DE-A 41 41 348. The reference discloses the attempt to make the signals, furnished by an optoelectronic sensor, accessible for controlling a windshield washer installation. Since a wiper device is necessary for reliable cleaning of the windshield, the passage of the windshield wiper over the sensor produces signals that adulterate the control signals for the windshield wiper motor. For acting upon the drive motor, only those signals that are generated by the sensor shortly after the last wiping passage over it until a new wiping cycle is initiated are used, that is, the signals generated during the passage of the wiper over the sensor are ignored. Wetting gradually reduces the constantly present signal until a reference value corresponding to the state of the windshield fails to be attained, which causes tripping of the wiper. The reference value is re-furnished continually, so that the signals caused by wetting are filtered out of the high noise level. Individual droplets cannot be detected in terms of size.

A programmable interval switch is also known in the prior art. In such an arrangement the driver actuates the interval switch as a function of his loss of visibility caused by the wetting. The time between two actuations is measured and subsequently used as the time interval.

SUMMARY OF THE INVENTION

Based on the prior art, it is the object of the present invention to create a simple, economical arrangement for utilizing the signals furnished by the sensor to control a windshield wiper installation.

The above object is attained by the implementation of a counter arrangement having a counter for detecting the signals caused by a passage of the wiper over this sensor. The counter counts the signals communicated by the sensor during a wiper operation. If a certain threshold value of the counter is exceeded, a further wiping operation is tripped. The threshold value is at least greater than the number of signals generated by the sensor while the wiper passes over the sensor, and can be reset to a starting value.

In German Utility Model DE-GM 93 09 837 corresponding to part of the subject matter of co-pending U.S. patent application Ser. No. 08/578,658, an optoelectronic sensor is described in which a plurality of measured sections are acted upon in clocked fashion, and the thus-furnished clocked signals are corrected via a subsequent evaluation device as a function of a time constant. As a result, it is possible to eliminate external factors, such as an extraneous radiation superimposed on the radiation of the arrangement, so that only signals dependent on the wetting are produced. However, since, as a result of the above the noise level no longer plays any role in the input signals, each film and each wetting is necessarily clearly associated with the signals, that is, each film and each wetting necessarily corresponds with the droplet size and quantity. As a result, the signal itself, which is analogous to the wetting, can be used to control the windshield wiper. Instead of a time slot of the kind required in the prior art for fading out the signals caused by the windshield wiper, the entering signals can thus be evaluated over the entire period of time. There is no need to evaluate the incoming input signals in terms of amplitude. Rather it suffices merely to count the number of signals (i.e. of arriving droplets). The passage of the wiper over the sensor, which also generates signals, is taken into account quite simply by providing that signals for controlling the windshield wiper motor do not exist until the number of signals is greater than the signals of the sensor that can with certainty be said to be caused by the passage of the wiper over the sensor. The counter arrangement counts every pulse, so that with certainty, signals to be ascribed to wetting trip a wiping operation.

BRIEF DESCRIPTION OF THE DRAWINGS

The invention will be described below in terms of an exemplary embodiment, in conjunction with the accompanying drawings. Shown are in.

THE INVENTION

Figure 1:
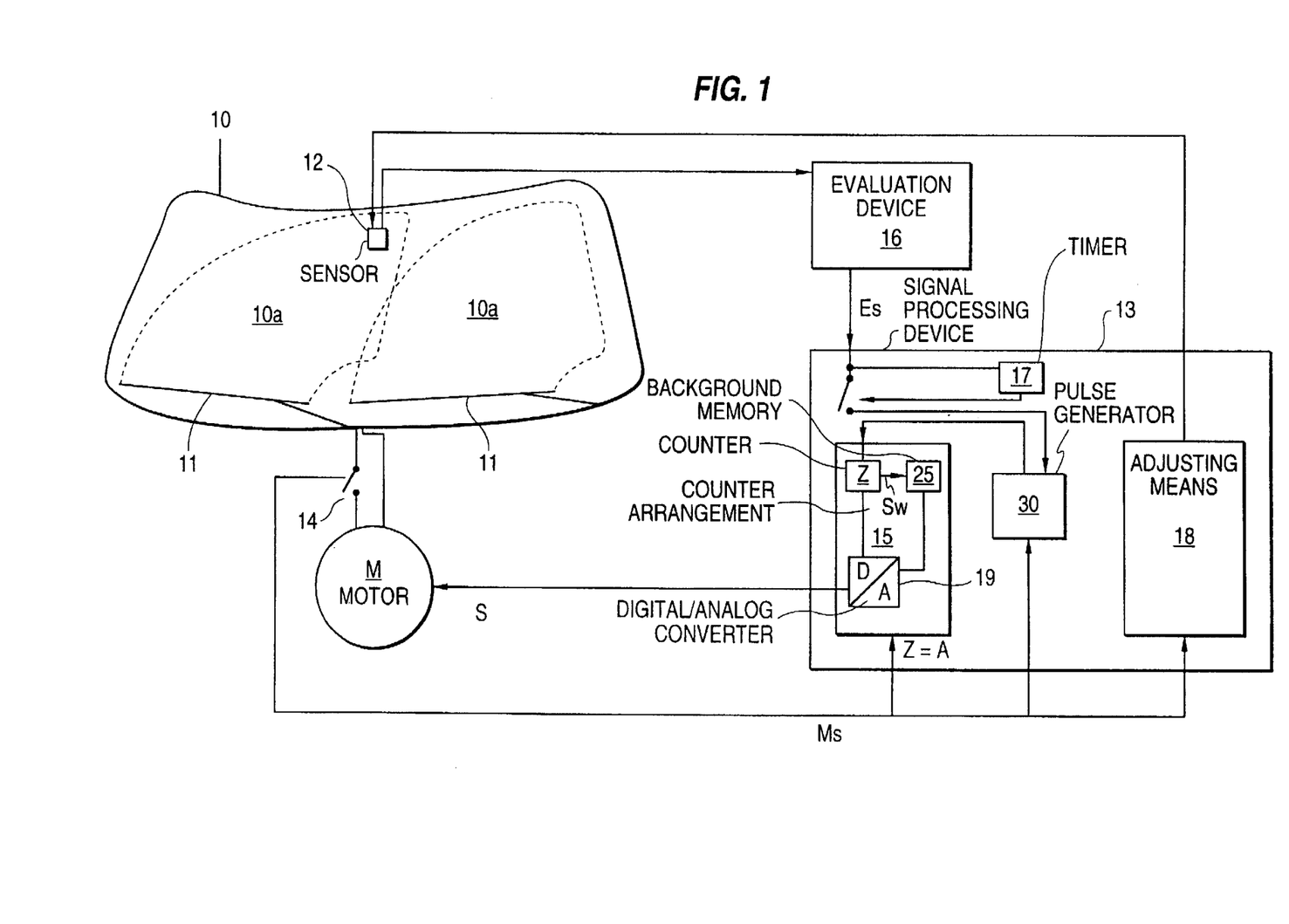
FIG. 1 a schematic circuit arrangement of the device for controlling a windshield wiper installation.

In FIG. 1, a device for controlling a windshield wiper installation has a drive motor M, which guides at least one wiper, and usually two wipers 11, over a wiping area 10a of a windshield. A sensor 12 of the kind known from co-pending U.S. patent application Ser. No. 08/578,685, is disposed in the wiping area 10a. For a detailed description of this sensor, one may refer largely to the above U.S. patent application. However, the details of the sensor will be discussed below as needed.

The wiper 11 passes over the sensor 12 is passed over at least once during a wiping operation. If the sensor is disposed peripherally, and if it is disposed in some arbitrary point in the wiping area of the wiper, it is passed over twice. The sensor is responsive to a wetting of the windshield in such a way that any influence on the sensor generates a signal Es corresponding to the droplet size or droplet quantity. A signal processing device 13 is coupled with the drive motor M with the sensor 12 and converts the signals generated by the sensor 12 into control signals S for the drive motor M. The device may also include a switch contact device, which may optionally be associated with at least one certain position of the wiper during the wiping operation. Typically, the switch contact device 14 is the end switch of the drive motor M, upon whose actuation the wiper 11 is placed in its parking (i.e. non-action) position.

As a means for detecting the signals that are generated by the sensor 12 while the wiper 11 passes over it, the counter Z of a counter arrangement 15 is provided. The counter counts all the signals furnished by the sensor 12 during a wiping operation and compares them with a preset threshold value. Exceeding this value trips a wiping operation. The preset threshold value is greater, than the number of signals generated by the sensor 12 during the passage over it of the wiper. After the next wiping operation is tripped, but no later than after at least one wiping cycle, the value of the counter arrangement 15 is reset to a starting value. A switch contact device can also emit a signal as soon as the wiper is in its parking position, for instance.

In the exemplary embodiment, the sensor itself operates optoelectronically, that is by a collaboration of radiation sources and radiation receivers. The source and receivers are part of at least two measured sections, which are triggered in alternation via a clock generator. An evaluation device 16 detects the clocked signals, and the arriving signals are corrected to zero via a time constant, as described in co-pending U.S. patent application Ser. No. 08/578,685. As a result of the above, it is possible to blank out even strong extraneous radiation so as to produce signals Es that are dependent only on the film and wetting present on the windshield 10. What is essential is the capability of the sensor 12 to generate signals which correspond to the droplet size and quantity, regardless of the mode of operation of the sensor (optical, capacitive, etc.). Small droplets generate small signals and large droplets generate large signals, and, if the droplets are in motion in the wind they even generate a plurality of signals, so that the quality and quantity of the wetting can be clearly distinguished. While wiping is done according to the prior art as soon as a certain reference value fails to be attained, in the above arrangement the response performance can be regulated within the usable signal range analogously with the course over time of re-wetting, while the detection threshold D, for instance, is not varied. An adjustment arrangement or adjusting device adjusts a radiation output of the various radiation sources and is dimensioned such that when the sensor-active surface, that is, a surface on the windshield adapted to reflect at least a portion of the radiation generated by the radiation sources, is not wet (i.e. in a rest state), each measurement section generates a part of the detection signal. A mean amplitude value of the detection signal is equal to the mean amplitude value of the segments of the detection signal associated with the other measured sections, and a filter circuit filters the clocked detection signal with respect to the difference between the part of the detection signal associated with the various measured sections, to generate a control signal. The details of the above arrangement are set forth in U.S. patent application Ser. No. 08/587,685. The sensor, evaluation device, clock generator, adjustment arrangement and filter circuit together form an exemplary version of a sensor system as described above.

Figure 10:
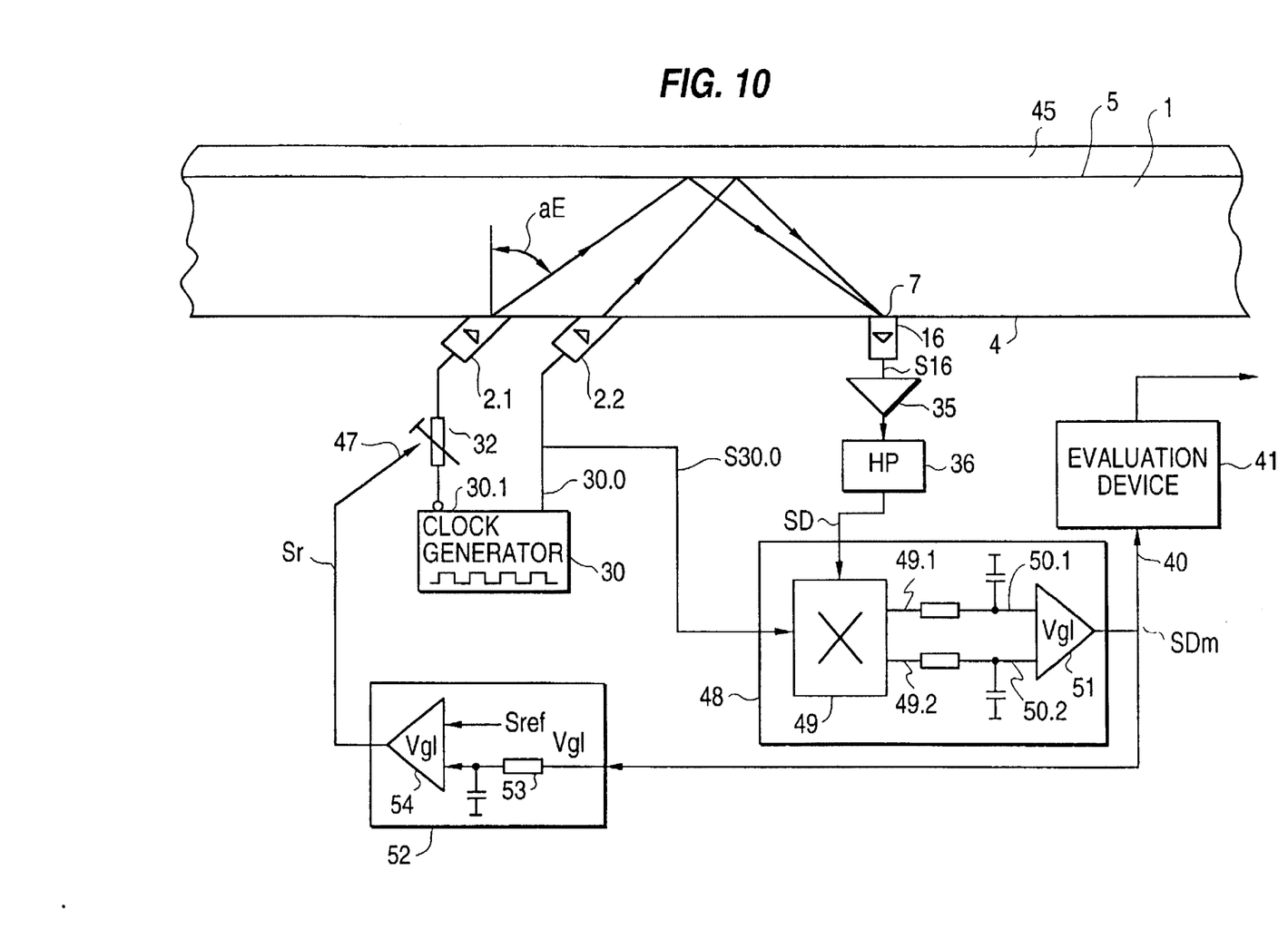
FIG. 10 a block circuit diagram of the sensor.

In the arrangement shown in FIG. 10, the switch arrangement for controlling the two radiation sources 2.1 and 2.2 is a pulse generator 30, which generates a current pulse alternatingly at a non-inverting output 30.0 and at an inverting output 30.1 for exciting the emission of the radiation source, connected to the output, of the pulse generator for the duration of the current pulse. To adjust the current value, the one output of the current pulse generator 30 includes a current adjusting member 32, which can be adjusted by means of an adjustment signal Sr at its adjustment input 47. The reflection of these two radiation sources at the coupling point of the radiation receiver 16 is converted by the receiver into an electrical output signal S 16, which reaches the output of the filter circuit 36 as a detection signal SD via an amplifier 35 and a high-pass or band-pass filter 36 in accordance with the arrangement shown in FIG. 3. A signal centering stage 48 is connected to the output of the filter circuit 36, which stage impresses the changes of the detection signal SD on the output of the filter circuit 36 of a midrange voltage Uz. In the exemplary embodiment shown, the signal centering stage 48 includes a synchronous demodulator 49 with two demodulator outputs 49.1 and 49.2, each of which is associated with a radiation source. The association is carried out via a control pulse S 30.0 of the current pulse generator 30, which also controls the emission of the radiation sources. In the exemplary embodiment shown, the demodulator outputs 49.1 and 49.2 are followed by demodulation value memories 50.1 and 50.2 which momentarily store the average amplitude value of the signal parts of the demodulation signal SD, which parts are scanned by the synchronous demodulator 49 and are associated with both radiation sources, and in this manner constitute an envelope demodulator. The difference value is formed from the momentary, average amplitude values of the two detection value memories in an adjoining operational amplifier 51 and impressed on a mean value. The smoothed detection signal SD m formed in this way, which is essentially freed from interferences in comparison to the detection signal SD at the output of the filter circuit 36, is supplied to both an evaluation device 41 and a regulating circuit 52 having a high control time constant Tr. In the exemplary embodiment shown, the regulating circuit includes a time constant member 53 and a comparator 54, which generates an adjusting signal Sr for the adjusting input 47 of the current adjusting member 32 from the comparison with a reference signal Sref. The above is effected such that the radiation output of the radiation source 2.1, which is regulated by means of the current adjusting member, is changed so that the difference of the detection amplitude values at the output of the signal centering stage 48 approaches zero. The regulating speed, i.e. the control time constant Tv of the regulating circuit 52, is calculated in this connection so that it is essentially many times greater than the slowest changes of a wetting process to be detected.

On the input side, the evaluation device 41 can also be directly connected to the output of both detection value memories 50.1 and 50.2, in particular when the wetting is intended to be measured by means of the evaluation device. The control time constant is essentially many times greater than an oscillation period of the switching sequence signal, which switches the radiation sources or groups of radiation sources associated with the radiation receiver. As a result, slower or lasting changes in the sensor-active surface of the windshield, which were not caused by the wetting or do not concern it, are not taken into account when detecting or measuring the wetting, and influences, which result from change, dirt accumulation, or temperature differences and which cause problems for known systems, can be easily eliminated.

Figure 6:
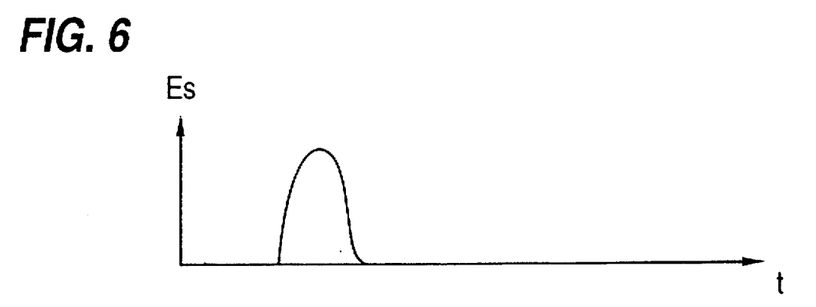
FIGS. 6–8 curves in which the value of an input signal is plotted versus time, if an insect, a water droplet, and a wind-driven water droplet, respectively, strike the windshield.
Figure 7:
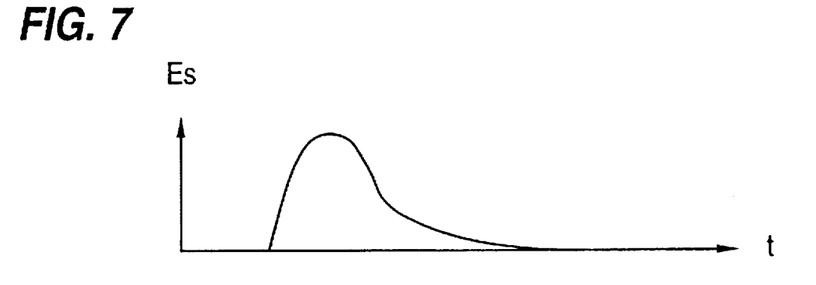
Figure 8:
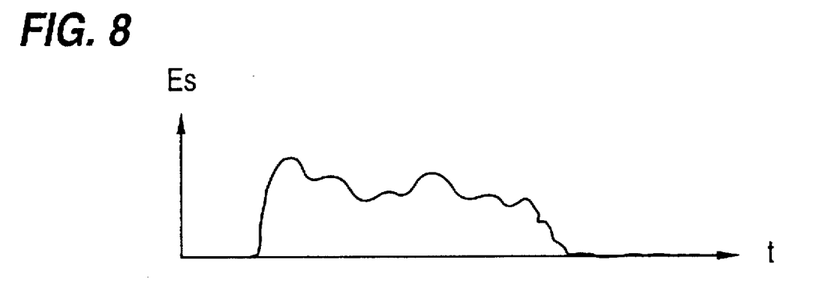

The values furnished by the counter Z can then be supplied directly to a digital/analog converter 19, which uses those value to generate control signals S for the drive motor M. It can be generally assumed that the higher the counter state, that is, the higher the number of signals counted by counter Z, either on average or at the onset of a wiping operation, the more often wiping is done. Evaluating all the signals during one wiping operation can be done without difficulty. By the automatic resetting of counter Z, either as a function of time or of control voltage or of the wiper position, even individually arriving signals are reliably throughout time. In the shown exemplary embodiment, to that end, the integral absolute difference between the starting value A and the threshold value (the exceeding of which threshold value trips the wiping operation) is set to be larger than the value corresponding to the number of times the wiper passes over the sensor, or in other words, the number 1 or 2, as applicable. Thus, if the sensor is disposed such that the wiper passes over it twice, then starting value A in the counter Z is set to be −2, and the threshold value may be set to be 2, such that the integral difference between A and the threshold value is 4, which is larger than the number of times the wiper passes over the sensor. The first sensor signal can then switch a timer, that raises the starting value or counter A by, 1 for a certain, for instance period of predetermined time; every further newly arriving signal, passed via the timer, occurring beyond the predetermined period of time then restarts the timer running time. The unequivocal capability of detecting the signals means that a single event, such as an insect striking the windshield as in FIG. 6, produces a clearly defined single signal, while even a droplet and certainly a wind-driven droplet, as shown in FIGS. 7 and 8, generates longer signals or a plurality of signals, which cause the counter to count correspondingly upward so that the preset threshold value is exceeded. This avoids unexpected tripping, which could startle the vehicle driver. It follows logically from the above that each subsequent sensor signal occurring during the predetermined time period further raises the counter state, and that the counter is reset to its starting value in the absence of any subsequent sensor signals after the first sensor signal during the predetermined time period.

Adjusting means 18 may be provided to regulate the response performance of the sensor 12. These adjusting means 18 may be disposed directly on the sensor and after a predetermined time $t_v$ after the beginning of a wiping operation reduce the response performance of the sensor as a function of the motor signal Ms of the switch contact device 14. This causes a shift in the value at which the existing signals begin to be detected. Within the individually present signals, control courses can thus be formed which already vary the value of the signals, corresponding to droplets, for evaluation purposes. Within usable signals, the detection threshold is shifted. As a result, with a reduced response performance, large droplets, because of the signal height and/or duration, lead to an input signal, while smaller droplets have no effect.

The above can be accomplished either by reducing the response performance and sensitivity of the sensor by regulating the sensitivity, thus producing signals that because of reduced amplification have a lower amplitude, or by regulating the control time constant, so that the signals are chronologically shorter. Alternatively, signals with a different divider ratio can be detected. A common feature of all these kinds of controls is that the adjusting means 18 for regulating the response performance of the device, after a predetermined time $t_v$, which may optionally also be zero, and after the wiper 11 has left its parking position or after the control signal has been transmitted to the wiper, regulates the response performance from a starting state of sensitive response performance to a predetermined intermediate state of non-sensitive response performance, and then within a certain time $t_2$ regulates it back to a final state, which preferably corresponds to the starting state. In this regard, a signal of the end switch can optionally be dispensed with.

Correction of the furnished signals in the sensor via the control time constant is done in principle such that the differential value of the signal tends to become zero; with a long control time constant, the differential value moves more slowly toward zero than with a short control time constant. During a wiping operation, the adjusting means 18 regulate the control time constant to be shorter than at a time during which no wetting is present, that is, in a rest state of the sensor active surface of the windshield. It is thus possible for variations caused by the self-drying streaks produced by the wiping to be blanked out of the measurement signals. The control time constant is regulated by the signal processing device 13, as a function of the signal of the motor end switch 14 and of a period of time of approximately 10 to 30 seconds. The sensitivity is thereby shifted such that after regulation to the starting state, only large droplets are detected. As a side effect, a signal generated by the passage of the wiper 11 over the sensor 12 may be evaluated, because when there is heavy rain a large wiping pulse is also generated.

As an alternative, or in addition, control means 30 can also be provided, which as a function of a signal of the switch contact device 14 reduce a divider ratio within a predetermined period $t_2$ down to 1:1, so that initially a plurality of signals Es lead to a single signal, until the control means 30 have set the divider to 1. As a result, either from rain or from relatively large droplets, which generate a plurality of signals because of their motion in the wind, one signal is created from a plurality of signals despite the initially high divider, or one signal is created as soon as the divider has been reduced after a certain period far enough that a single signal is transmitted onward.

Figure 2A:
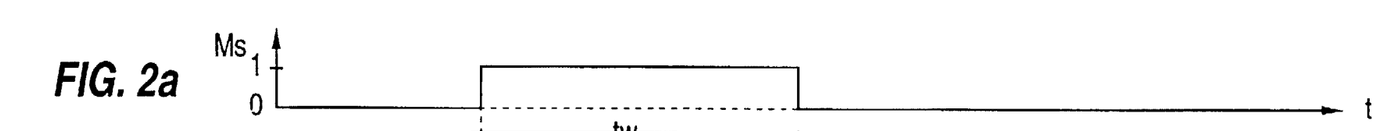
FIGS. 2a, 2b, 2c, curves representing motor signal, input signal and counter position versus time.
Figure 2B:
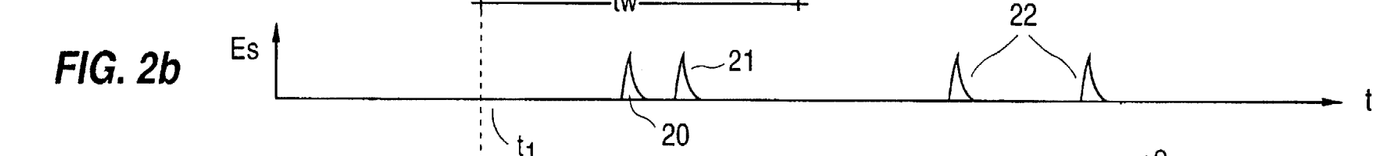
Figure 2C:
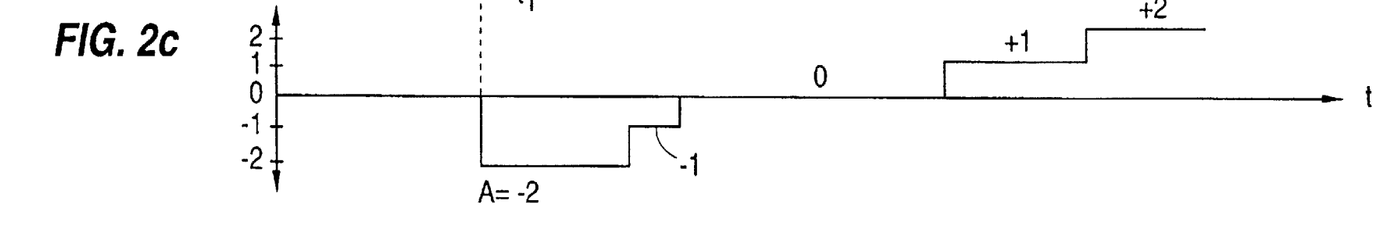

The results obtained will now be described in further detail in conjunction with FIGS. 2a–5. FIG. 2a first shows the motor signal Ms, which varies over time $t_w$. As soon as the windshield wiper motor is switched on at time $t_1$, a motor signal Ms is produced, which is present over the wiping time period $t_w$. The appearance of this motor signal assures that the value of the counter Z is set to the starting value A, which according to FIG. 2c is −2. The number, −2, is chosen whenever the wiper 11 passes twice over the sensor 12 in the wiping area 10a. In FIG. 2b, signals that occur over time are also plotted. The first two signals 20 and 21 are brought about when the wiper passes over the sensor. Each signal leads to one pulse, as an input signal Es, into the signal processing device 13. From these two signals alone, the counter arrangement 15 counts upward to the value zero, which matches the preset certain value. The two signals 22 that also occur then raise this value farther, so that as a function of the value of the counter Z, the digital/analog converter 19 now generates control signals S for the drive motor that in turn cause the wiper to be switched on, the consequence of which is resetting of the counter to the starting value of −2.

Figure 3A:
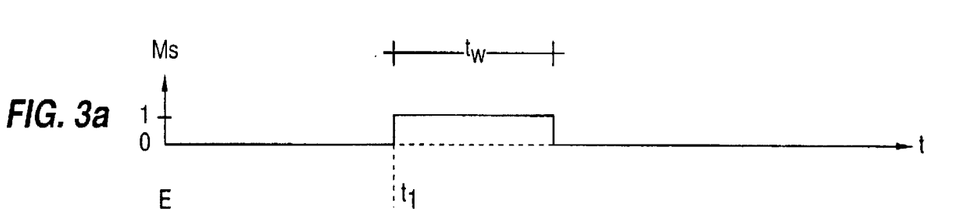
FIGS. 3a, 3b, curves representing motor signal and sensitivity versus time.

This counter arrangement 15 can be used together with sensitivity control, as can be seen from FIGS. 3a–5. The examples show a closed-loop control of sensitivity, or in other words a reduction in amplitude. Varying the control time constant or divider ratio, however, has a similar effect. In FIG. 3a, the motor signal Ms is plotted; at time $t_1$, via the adjusting means 18 for regulating the response performance, it regulates the sensitivity E from a maximum value $E_{max}$ to a minimum value $E_{min}$ as shown in FIG. 3b. This minimal value is initially maintained over a predetermined time $t_v$, as shown in FIG. 3b. In a time period $t_2$ following the wiping operation, which in practice may be from 10 to 30 seconds long, for instance, the sensitivity E is gradually returned to the value $E_{max}$.

Figure 3B:
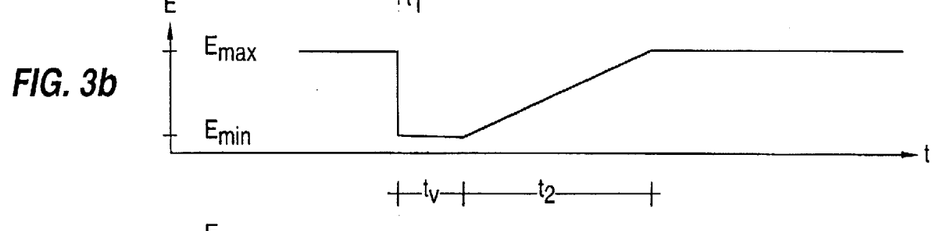
Figure 4:
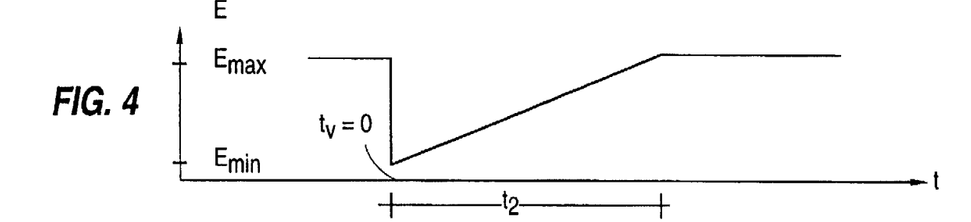
FIG. 4 a curve representing sensitivity versus time at $t_v=0$.

As shown in FIG. 4, as an alternative to the option shown in FIG. 3b, the possibility exists at $t_v = 0$ to allow the response performance to gradually continually increase during the entire wiping time $t_w$. Over the entire time period, the continuously furnished signals are supplied to a memory, which trips a subsequent wiping operation if a preset value is exceeded. As a result, in a heavy rain, signals that enable sensitive control of the windshield wiper installation are furnished during the entire wiping operation. To attain fast response of the windshield wiper control, as needed for instance when passing a truck or emerging from a tunnel, the possibility also exists of loading signals, which have occurred shortly after the wiping operation, directly into the memory of the control unit 15 to control the windshield wiper installation.

Figure 5:
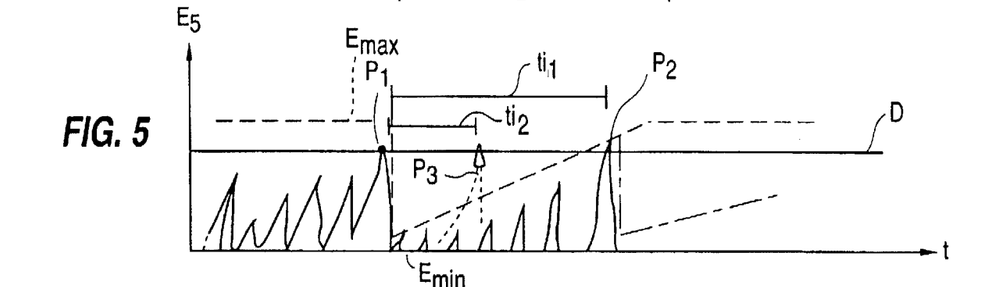
FIG. 5 a curves representing input signals versus time.

The result of the above is shown in FIG. 5. As described above, the sensitivity, or in other words, the response performance of the entire sensor is varied in regulated form as indicated by the dashed line. Signals lead to a reaction of the control system as soon as the detection threshold is exceeded, and a plurality of signals can also be stored in a memory in order to achieve a gentle, uniform course of wiping. At time $t_b$ on the left-hand side of FIG. 5, rain starts up; at the peak P1 it trips wiping, since the detection threshold D is exceeded. The vehicle user would have also actuated his wiper now because of the hindrance to vision. At $t_v=0$, the sensitivity at the beginning of the wiping operation, that is, at time $t_1$, is lowered from the starting state to an intermediate state as shown. As a consequence, the droplets which will follow will appear smaller in amplitude. If a heavy rain is involved, then the signals would nevertheless immediately reach the detection threshold D again. The sensitivity is gradually raised again and would regain a final state of maximum sensitivity $E_{max}$, which is equivalent to the starting state. However, with the presence of a droplet in the form of the peak P2 which exceeds the detection threshold, the sensitivity immediately drops, because of the re-tripped wiping operation, to the intermediate state of minimal sensitivity $E_{min}$. The time $ti_1$ between peaks or between the reduction of sensitivity is recorded by the control system as the next wiping interval, with the time interval $ti_1$. The variable conditions during a rain would be taken into account by providing that if the second peak had already reached the detection threshold earlier, an example being the peak P3 shown in dashed lines, the time interval $ti_2$ would have been the result.

The counter arrangement 15 may be a first memory unit, which, if a predetermined value V is exceeded, and/or after a predetermined number of wiping operations, possible succeeding one another within a certain period of time, transmits further signals Sw via signal transmitting means to a background memory 25, whose content also affects the generation of control signals, optionally also after unloading of the memory unit.

Figure 9:
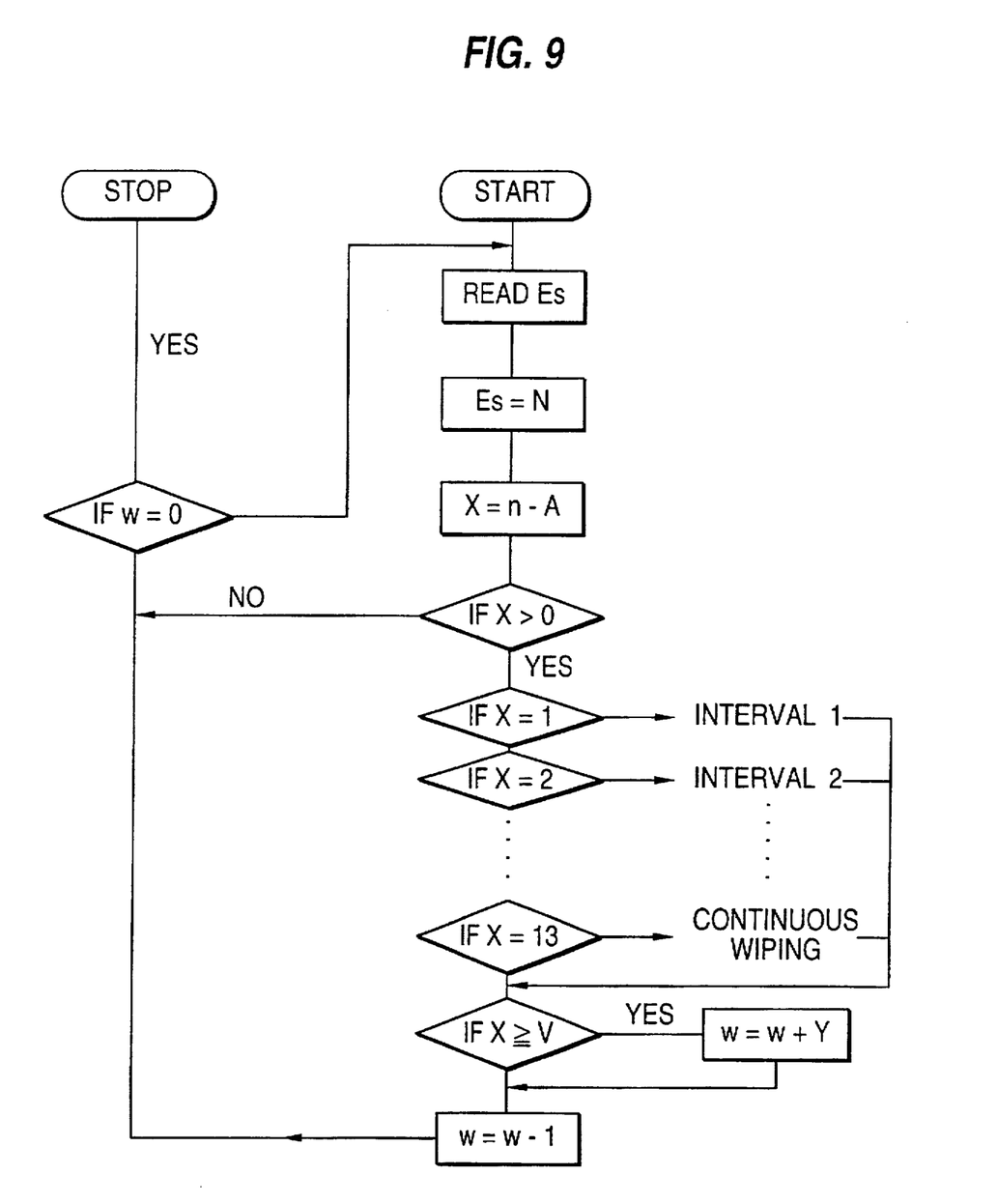
FIG. 9 a flowchart for operation with a background memory.

The schematic flow chart of such a device can be seen in FIG. 9. As soon as signals Es are furnished by the sensor, the counter arrangement, as a memory unit, is started by START. The input signals are written in and produce the integral number n. After subtraction of the starting value A, which for instance reflects the signals caused by the passage over the sensor of the wiper, the result is the actual number x of signals that have been input during one wiping operation. If this value x is less than zero, this can in principal cause termination of the wiping or prevent starting of the drive motor in the first place. If x is greater than 0, then depending on the number of signals briefly arriving, optionally during one wiping operation, either the interval circuit of the windshield wiper is tripped with a time interval dependent on the number of signals, or if there is a large number of signals, such as more than 13 of them, then continuous wiping is tripped immediately, for instance when passing a truck. At the same time, a check is made as to whether the value x is greater than a predetermined threshold value V; in addition or alternatively, the number of wiping operations immediately succeeding one another can also be used. If the value V is exceeded or attained, the value of the background memory 25 is raised, and preferably a value is chosen which is less than the total content of the memory, to attain flexible performance of this background memory. For instance, the value can be raised by 2. In an ensuing step, this value is then reduced by 1, for instance, as soon as a signal is output by the switch contact device.

Finally, a check is made as to whether instead of only x being equal to 0, the value of the background memory is also again 0. Not until both conditions are met does the drive motor stop.

By means of this background memory 25, a gradual simulation of the wiping motions is possible, since even in nature rain does not start and stop abruptly, and so regulated continued wiping after a rain is achieved. On the other hand, the memory unit acting in the foreground, in this case the counter arrangement, can act lightning fast to splashing water.

When the certain value of the counter (Z) is reached, for instance, its maximum value, the control unit learns that a corresponding wetting is present, which necessitates a further wiping operation. However, if this value is reached before the preceding wiping operation is ended, then wetting is present of such a nature that the wiper must remain in continuous operation. In this sense, this premature reattainment of the value causes such a slowing down, for instance, of the control signal (S) that the drive motor (M) remains in continuous operation. To that end, the time in which the control voltage is applied can for instance be varied accordingly.

We claim:

1. A windshield wiper arrangement comprising:
 a windshield having a wiping area and a sensor-active surface on its wiping area, the windshield further defining a reflective element corresponding to the sensor-active surface and a detection side disposed opposite the reflective element;
 a wiper disposed adjacent the windshield for sweeping over the wiping area during a wiper operation; and
 a wiper control system operatively coupled to the wiper and including:
 a drive motor for driving the windshield wiper to sweep over the wiping area, the drive motor having a control input;
 a sensor system including an optoelectric sensor disposed in the wiping area such that the wiper passes over the sensor n times during each wiper operation, n being equal to at least one, the sensor system being configured for generating sensor signals in response to an element coming into contact with the sensor-active surface in the wiping area, the sensor system and the windshield further being part of a means for indicating a change in the windshield, the means for indicating comprising:
 at least two measured sections for generating, reflecting and receiving radiation for measurement, each measured section including:
 a radiation source disposed adjacent the detection side of the windshield for generating radiation for transmission through the windshield thereby resulting in generated radiation;

a sensor-active surface on the reflective element for reflecting at least a portion of the generated radiation thereby resulting in reflected radiation emerging from the detection side of the windshield; and a radiation receiver disposed adjacent the detection side of the windshield at a distance from the radiation source for receiving the reflected radiation, the radiation receiver having an output for producing a detection signal representing received radiation;

a clock generator operatively coupled to the at least two measured sections for periodically actuating respective ones of the measured sections;

an adjusting device operatively coupled to the at least two measured sections for adjusting the detection signal so that, in a rest state of the sensor-active surface of each measured section, a part of the detection signal corresponding to each measured section has an average amplitude value equal to an average amplitude value of parts of the detection signal corresponding to other ones of the measured sections;

a filter circuit connected to the radiation receiver of each measured section for producing a filtered detection signal; and an evaluation device having an input for receiving the filtered detection signal and being operatively coupled to the signal processing device, the evaluation device producing the sensor signals in dependence of a difference between parts of the filtered detection signal corresponding to respective ones of the at least two measured sections;

a regulating device including:

a signal centering stage disposed at an output of the filter circuit for receiving the filtered detection signal therefrom, the signal centering stage having:

a synchronous demodulator for scanning an amplitude value of parts of the detection signal corresponding to each actuated one of the measured sections;

a demodulation value memory operatively connected to the demodulator for storing average amplitude values of the parts scanned by the demodulator; and a comparing device operatively connected to the demodulation value memory for generating a difference value of the average amplitude values stored by the demodulation value memory; and a regulation signal generator connected to an output of the signal centering stage and including:

a time constant member for generating a control time constant Tr; and a regulation signal generator operatively connected to the time constant member for generating a regulation signal Sr during time Tr from the difference value of the average amplitude values stored by the demodulation value memory, whereby the adjusting device is connected to the regulation signal generator for receiving the regulation signal therefrom, the regulation signal being effective for guiding an adjustment effected by the adjusting device such that the difference value of the average amplitude values approaches zero; and a signal processing device having an input coupled to the sensor signals and an output connected to the drive motor for producing control signals for the drive motor in dependence of the sensor signals, the signal processing device including a counter arrangement comprising:

a counter for counting the sensor signals thereby resulting in a counter state of the counter, the counter state of the counter further being equal to a predetermined starting value before each wiper operation;

threshold means coupled to the counter and responsive to the counter state exceeding a predetermined threshold value for producing control signals for the drive motor for tripping a further wiper operation, the threshold value being greater than n; and reset means coupled to the counter for resetting the counter state to its predetermined starting value.

2. The arrangement according to claim 1, wherein the wiper control system further includes timer means coupled to the threshold means for setting a time period for each wiper operation to be a set time period $t_w$, the threshold means being configured such that; if a counter state of the counter exceeds the predetermined threshold value within the set time period $t_w$ during a wiper operation, the threshold means effects a continuous generation of control signals for the drive motor for continuously driving the wiper.

3. The arrangement according to claim 1, further including an end switch operatively coupled to the wiper and to the reset means, the end switch being configured such that its actuation places the wiper in its parking position and actuates the reset means to reset the counter state to its starting value.

4. The arrangement according to claim 1, wherein an absolute difference between the starting value of the counter state and the predetermined threshold value is greater than n by at least one.

5. The arrangement according to claim 4, wherein the wiper control system further includes a timer operatively coupled to the sensor system and to the reset means, the timer being configured such that:

a first sensor signal at a time when the counter state is at its starting value starts the timer running for a predetermined time period and raises the counter state, the reset means further being configured to reset the counter state to its starting value in an absence of further sensor signals during the predetermined time period;

each subsequent sensor signal occurring after the predetermined time period restarts the timer to run for the predetermined time period; and each subsequent sensor signal occurring during the predetermined time period further raises the counter state.

6. The arrangement according to claim 1, wherein:

the element coming into contact with the sensor-active surface on the windshield comprises at least one droplet;

for each sensitivity of the sensor system, the sensor system is configured for generating a sensor signal representative of at least one of a size of the droplets and a quantity thereof; and the wiper control system further includes a sensitivity adjusting means for adjusting the sensitivity of the sensor system, after a start of each wiping operation and during a predetermined adjustment time period, from a predetermined starting sensitivity to a lower predetermined intermediate sensitivity during a predetermined time period $t_1$, and thereafter from the intermediate sensitivity back to a final sensitivity during a predetermined time period $t_2$.

7. The arrangement according to claim 6, wherein:

the sensitivity adjusting means is configured for regulating the sensitivity of the sensor system to be one of adjusted to and maintained at the intermediate sensitivity in response to the sensor signal reaching a predetermined detection threshold signal after a time period $t_i$ has passed from the start of a corresponding wiping operation within the adjustment time period; and the wiper control system further includes timer means coupled to the sensitivity adjusting means for setting a time interval between two consecutive wiper operations to be equal to $t_i$.

8. The arrangement according to claim 6, wherein the sensitivity adjusting means is configured to adjust the sensitivity of the sensor system by adjusting an amplification of the sensor signals by the sensor system.

9. The arrangement according to claim 6, wherein the sensitivity adjusting means is configured to adjust the sensitivity of the sensor system by adjusting the control time constant Tr.

10. The arrangement according to claim 6, wherein the sensitivity adjusting means includes a divider ratio control means for reducing a divider ratio within time period $t_2$ down to 1:1 for adjusting a plurality of sensor signals to a single signal, the control means further setting the divider ratio back to 1 at the start of each wiping operation.

11. The arrangement according to claim 1, wherein:

the counter arrangement comprises a first memory unit;

the predetermined threshold value is a first predetermined threshold value; and the wiper control system further includes:

a signal transmitting means; and a background memory unit operatively coupled to the counter arrangement by the signal transmitting means such that, when a given windshield condition is met, the signal transmitting means transmit a signal Sw to the background memory unit resulting in a background memory state w of the background memory unit, the given windshield condition corresponding to at least one of the counter state exceeding a second predetermined threshold value and successive wiping operations within a predetermined wiping time period exceeding a predetermined wiping threshold value, the background memory unit further comprising means for influencing a generation of control signals for the drive motor as a function of the background memory state w.

12. The arrangement according to claim 11, wherein the signal transmitting means are configured to transmit the signal Sw such that it results in a signal value Y being stored in the background memory unit, the signal value Y being smaller than a maximum memory content of the background memory unit.

13. The arrangement according to claim 11, wherein:

the element coming into contact with the sensor-active surface on the windshield comprises a plurality of droplets; and the background memory unit is adapted to regulate continued wiping after the droplets have stopped coming into contact with the windshield.

14. The arrangement according to claim 11, wherein the means for influencing includes unloading means operatively coupled to the threshold means for unloading the background memory state w by a predetermined unloading value until w is completely unloaded.

15. The arrangement according to claim 6, wherein the final sensitivity is identical to the starting sensitivity.

* * * * *